United States Patent [19]

Dennehey et al.

[11] 4,417,890
[45] Nov. 29, 1983

[54] ANTIBACTERIAL CLOSURE

[75] Inventors: T. Michael Dennehey, Arlington Heights, Ill.; Charles K. Peterson, Fontana, Wis.

[73] Assignee: Baxter Travenol Laboratories, Inc., Deerfield, Ill.

[21] Appl. No.: 293,807

[22] Filed: Aug. 17, 1981

[51] Int. Cl.³ .............................................. A61M 3/00
[52] U.S. Cl. ................................... 604/256; 604/283; 604/905
[58] Field of Search ............... 128/247, 213 A, 213 R, 128/214 R, 214 C, 214 G, 214.2, 274, 224, 348; 285/DIG. 2, 352, 423; 215/316, 6

[56] References Cited

U.S. PATENT DOCUMENTS

| | | | |
|---|---|---|---|
| 3,416,567 | 12/1968 | Von Dardel et al. | 128/214 G |
| 3,633,586 | 1/1972 | Sheridan | 285/DIG. 2 X |
| 3,880,401 | 4/1975 | Wiltse | 128/214 R X |
| 3,918,450 | 11/1975 | Patel | 128/247 |
| 4,162,092 | 7/1979 | Hayes | 285/423 X |
| 4,187,846 | 2/1980 | Lolachi et al. | 128/214 R |
| 4,209,013 | 6/1980 | Alexander et al. | 128/247 X |
| 4,256,106 | 3/1981 | Shoor | 128/247 |
| 4,294,250 | 10/1981 | Dennehey | 128/247 |
| 4,340,052 | 7/1982 | Dennehey et al. | 128/247 |

FOREIGN PATENT DOCUMENTS 1193759 6/1970 United Kingdom ............... 128/247

Primary Examiner—Richard J. Apley
Assistant Examiner—Michelle N. Lester
Attorney, Agent, or Firm—Paul C. Flattery; Garrettson Ellis; Thomas A. Kmiotek

[57] ABSTRACT

A closure system for a conduit defining a connector at its end is provided having increased convenience of use and reliability of sterile sealing. A tubular closure member is provided which may be positioned about the connector in telescoping relation. The closure member surrounds but is spaced from the forward portion of the connector to provide space for antiseptic to be provided, to flow both inside of the connector member and about preferably at least 0.5 centimeter of the exterior forward portion thereof for improved antibacterial effect on the connector. An end closure such as a screw threaded cap may be provided.

17 Claims, 6 Drawing Figures

ANTIBACTERIAL CLOSURE

TECHNICAL FIELD

The present invention relates to an improvement in antibacterial closures which typically enclose a connector positioned on the end of a flexible conduit, with a liquid antiseptic such as povidone iodine being positioned within the closure to bathe the connector in antiseptic for antibacterial effect during storage. The connector is presently contemplated for use for connecting solution containers, sets, and catheters in peritoneal dialysis procedures. However, the contemplated use is by no means limited to such a field. It is contemplated that the connector of this invention may be used in any medical or other procedure where a connection is desired which comes as close as possible to a sterile connection.

At the present time thousands of patients who have no or limited kidney function due to end stage renal disease are being maintained by one of several types of artificial kidney dialysis. While many are maintained by hemodialysis, others are maintained by a medical procedure known as continuous ambulatory peritoneal dialysis (CAPD) described in U.S. Pat. No. 4,239,041. This latter technique is rapidly growing in clinical acceptance.

In the CAPD procedure, peritoneal dialysis solution is inserted into the peritoneal cavity, whereby diffusion exchange takes place between the dialysis solution and the blood in the blood vessels in the peritoneum, the natural body membrane which defines the peritoneal cavity. The waste products which are normally excreted through the kidneys, such as sodium ahd chloride ions, and other materials normally excreted by the body such as urea and creatinine, and also water, diffuse across the peritoneum and into the dialysis solution.

In the CAPD procedure, connections between dialysis solution containers and administration sets which communicate with a peritoneal catheter must be made and broken, normally several times a day. Particularly when the patient is doing his own CAPD exchanges, there is the possibility that the sterility of the flow path between the various solution containers and the peritoneal cavity may be compromised by airborne bacteria or the patient accidentally brushing a finger or a contaminated article across the open connector. The result of such a break in sterility can be peritonitis.

BACKGROUND ART

A closure system particularly for peritoneal dialysis catheters is currently marketed by the Quinton Instrument Company under the name Beta-Cap and Beta-Cap II. In this closure system, a self-sterilizing luer lock cap and adaptor is provided in which a handle member is positioned just behind the connector, and a cap with a stylet projects into the bore of the catheter. The catheter or set is temporarily sealed, typically with a clamp a short distance away from the connector. The bore of the connector is filled with an antiseptic such as povidone iodine. The cap is applied, with the stylet forcing antiseptic from the bore outwardly to spill about the outer surfaces of the connector as the cap is secured into sealing relation, and the connector is stored in this manner until it is ready for use.

A possible disadvantage of this system is the insertion of a stylet and an antiseptic tube into the bore of the catheter or set. The catheter or set before disconnection or uncapping is generally essentially sterile in its interior. Furthermore, antiseptic is applied with a needle-nosed tubular applicator which reaches down into the bore of the connector and tubing as close to the clamp as possible. The applicator is then withdrawn as the antiseptic is dispensed. The use of a non-sterile, needle-nosed applicator introduces contamination that otherwise would not be there.

The projecting, exposed stylet of the cap must pass through the atmosphere, where it possibly may pick up contamination. Accordingly, the very act of inserting the stylet or antiseptic applicator into the bore of the catheter or set may drive contamination into the bore.

At the same time, there is no guarantee that an air bubble where antiseptic has not reached will not remain in the bore of the catheter or set. This does not necessarily represent a serious problem, since the catheter or set starts out substantially sterile, and it is to be expected that the inner wall, in contact with an internal air bubble fairly deep within the set, will remain so. However, the stylet driving into the bore may well drive contamination into the air bubble, where it is not as effectively dealt with by the antiseptic in the system.

Furthermore, the outer surfaces of the connector in the above-described closure system may not be sterilized. Particularly in the event where screw threads are used it would be desirable to have a system to permit the substantial sterilization of that area by thorough contact with flowing liquid antiseptic.

Quinton U.S. Pat. No. 3,484,121 discloses a cannula extension and connector apparatus for the connection of two catheters and the like. The use of antiseptic is not taught therein.

The word "sterile" as used herein is intended to include not only its accustomed meaning of a total absence of living microorganisms, but also is intended to include the concept of substantial sterility, in which the number of microorganisms is reduced to such a low population that the likelihood of infection or contamination, i.e., peritonitis in the case of CAPD, is substantially reduced or eliminated.

DISCLOSURE OF INVENTION

In accordance with this invention, a closure system for a conduit defining a connector at its end is provided, having increased convenience of use and reliability of sterile sealing.

A tubular closure member may be sealingly positioned about the connector in telescoping relation. The closure member surrounds but is spaced from a forward segment of the connector to provide space for antiseptic to be provided, to flow both inside of the connector member and about preferably at least 0.5 centimeter of the exterior forward segment thereof for improved antibacterial effect on the connector.

An end closure may be provided to sealingly close the forward end of the tubular closure member. The end closure may be a removable, screw threaded cap or the like if desired. Alternatively, the end closure may be made integral with the tubular closure member.

In one embodiment, the desired connector for use herein defines an exterior circumferential annular shoulder face and, if desired, exterior circumferential front and rear shoulder faces.

A hollow, tubular handle member may be provided comprising a pair of hinged halves which are proportioned to close about the rear portion of the connector in surrounding relation. A forward portion of the handle member may define screw thread means, and the handle member may be proportioned to sealingly press against the rear annular shoulder face. Accordingly, this handle member may be easily applied to a connector member at the end of a conduit when the other end of the conduit is secured, for example, to a peritoneal dialysis catheter or the like, since the hinged halves can open up and then close about the rear portion of the connector.

The handle member may also serve as a strain relief member to prevent excessive bending strain of the conduit, resulting in its deterioration. The conduit carries a rigid connector. The point where the rigid connector ends thus can focus excessive strain in the flexible tube immediately adjacent to the rigid end of the connector as the tube bends. The combined handle member and strain relief member may surround this strained portion of the flexible tube and provide a flared aperture through which the flexible tube extends to distribute the strain of bending of the tube over a wider area. Also, it may be desired for the handle member to be relatively flexible, being made of silicone rubber or the like, for further distribution of the strain.

To apply the closure system of this invention, one closes the bore of the conduit at a point spaced from the open end and substantially fills the bore from the open end with liquid antiseptic, enclosing the conduit end with a sealed housing in accordance with this invention which surrounds, but is spaced preferably at least 0.5 cm. from the end of the conduit, without physically penetrating the bore with any portion of the sealed housing. As the result of this, antiseptic can flow between the bore and the space between the housing and conduit end for antibacterial effect within the bore, and also at the outer surface of the endmost portion of the conduit. One can also add antiseptic to the space between the housing and the endmost portion, then closing the housing with a cap or the like for antibacterial storage of the conduit end.

DESCRIPTION OF SPECIFIC EMBODIMENT

Figure 1:
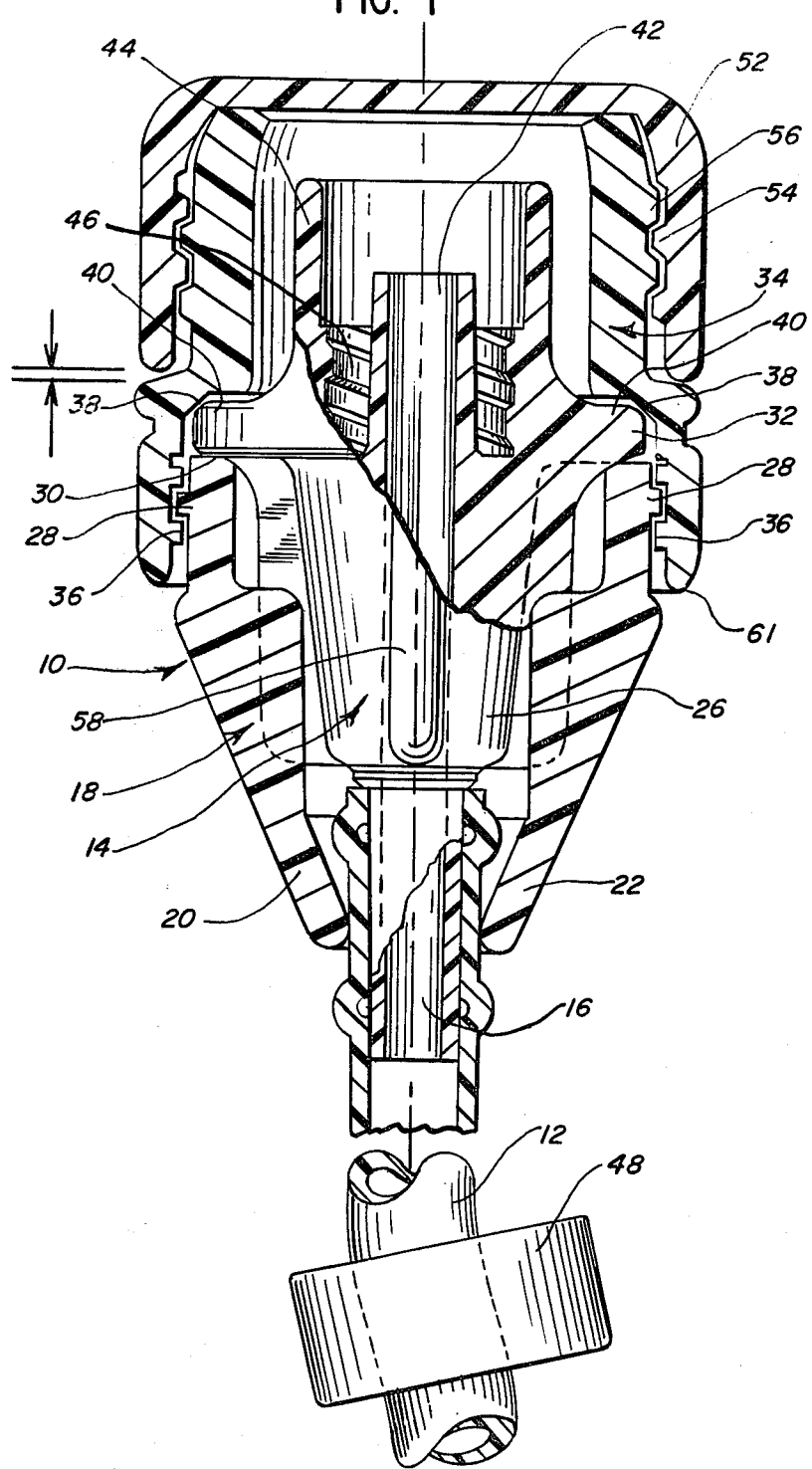
FIG. 1 is a longitudinal view taken mostly in section of one embodiment of the closure system of this invention, in place surrounding a connector on the end of a flexible conduit.
Figures 2, 3:
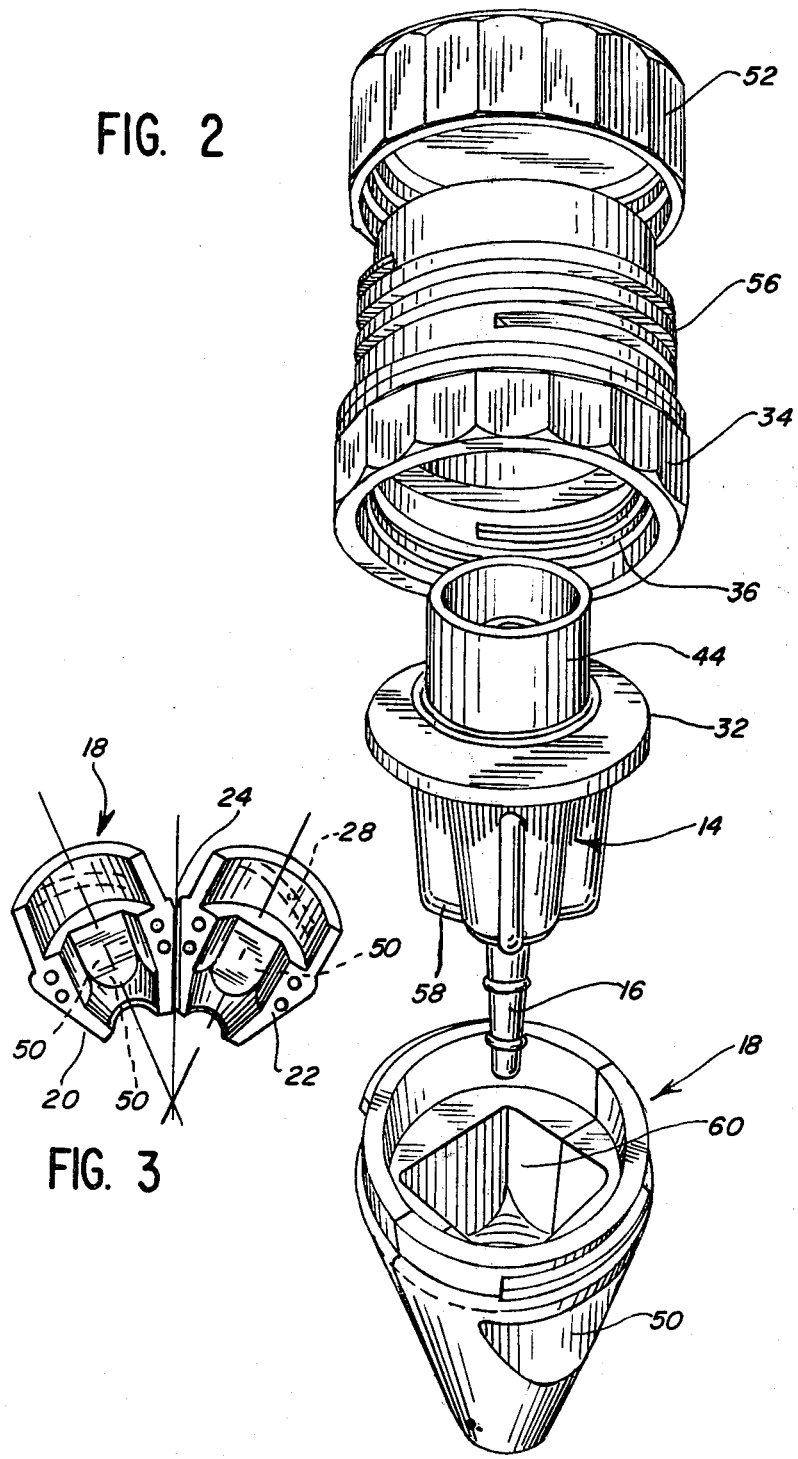
FIG. 2 is an exploded perspective view of the closure system of FIG. 1.
FIG. 3 is a perspective view of the hollow tubular handle member utilized in the closure system of FIG. 1.

Referring to FIGS. 1-3, a first embodiment of the closure system 10 of this invention is disclosed. Flexible conduit 12 defines a connector 14 at its end, being connected to the flexible tubing or conduit 12 by projecting tube 16 which fits telescopically into the end of flexible tubing 12 by an interference fit as shown, by means of solvent sealing, heat sealing, or the like. Tubing 12 may be made of polyvinyl chloride plastic for example, while the other materials of the connector member may be made of an appropriate rigid, plastic material.

Hollow, tubular handle member 18 comprises a pair of hinged halves 20, 22 connected by integral hinge 24 and proportioned to close about the rear portion 26 of connector 14. Handle member 18 may be a single, molded piece of plastic, for example polypropylene, with hinge 24 being an integral part thereof and defining a well known "living" plastic hinge. Also, snap-fit means may hold the handle 18 closed.

Handle member 18 also defines screw threads 28 at its forward portion, and is proportioned at its forward end to press against the rear annular face 30 of a shoulder 32 defined by connector 14 so that an annular seal may be provided, if desired.

Tubular closure member 34 is also provided, with the rear end of the closure member defining screw threads 36 which are proportioned to mate in closing relation with screw threads 28 of handle member 18, as shown in FIG. 1, Also, closure member 34 defines an inner annular seat 38 sealingly pressing against front annular shoulder face 40 of connector flange 32 when in closing relation with the handle member to provide an annular seal area, which may be the primary seal area. It can be seen particularly that the inner annular seat 38 may define an acute angle of about 45° with the longitudinal axis of the connector to provide a seal area with front annular face 40 of relatively small area so that, as tubular closure member and the handle member are screwed togetherin relatively tight manner, a higher sealing pressure is exerted in the annular seal than in the circumstance where the annular seal area would be of larger area.

Connector 14 may define an internal projecting sleeve 42 and an external sleeve 44, positioned to extend beyond internal sleeve 42 in spaced, coaxial relation therewith. Screw threads 46 are provided on the inner surface of sleeve 44, or optionally the external surface of sleeve 42, for mating with a connector of cooperating shape for a sealed connection. Such a threaded structure is per se known to the art.

Pinch clamp 48 of conventional design is provided to releasably clamp the bore or lumen of tube 12 as the connector is assembled.

Handle member 18 may define a pair of opposed, flat exterior faces 50 proportioned to facilitate manual grasping thereof, for entering into tight, connecting relation with tubular closure member 34 to provide a reliable seal.

Screw threaded cap member 52 may be provided with mating screw threads 54 to match the screw threads 56 of closure member 34 for sealing of the top.

Handle member 18 may be closed around the rear of connector 14, and the tubular closure member 34 of this invention may be applied to surround connector 14. However, prior to adding cap member 52, it is preferred to add a liquid antiseptic such as povidone iodine to the bore of inner sleeve 42 so that the antiseptic runs through the interior of connector 14, being restricted in its downward flow by pinch clamp 48. Antiseptic solution is also preferably added to both interior and exterior sleeves 42 and 44 for complete antibacterial action on all surfaces.

Following this, cap 52 is added to contain the povidone iodine or other antiseptic.

As shown, the endmost portion of the conduit defined by tubing 12 and housing 14 is sleeve 44. The housing formed in accordance with this invention surrounds it, but is preferably spaced from at least 0.5 cm. from the endmost portion as shown to provide a chamber in which liquid can reside and flow for antibacterial action.

The closure is stored in this manner, with the leakage of antiseptic being prevented by the tight seal between members 34 and 40 at seal area 38, for prevention of bacterial growth and the closest possible approximation to sterility in the vicinity of sleeves 42, 44.

When it is desired to use the connector, cap 52 may be opened, and the connector inverted to allow the antiseptic to run out. After the antiseptic has drained, one may remove member 34. A connection with another mating connector may be made, and pinch clamp 48 and handle 18 may be removed. Prior to the removal of pinch clamp 48, the newly formed connection may be subjected to another bactericidal technique if desired, for example exposure to ultraviolet radiation or the like.

Vanes 58 of connector 14 are proportioned to fit into the corners 60 of the hollow interior of handle member 18, for retention of the connector 14 in nonrotatable relation with handle member 18.

The bottom skirt 61 of tubular closure member 34 is generally free from contact with handle member 18 so that the entire weight of the sealing pressure can be borne at the inner annular seat 38 and annular shoulder face 40 between members 34 and 14, with a second seal being optionally provided as stated at the forward end of handle member 18 and rear face 30.

Figure 4:
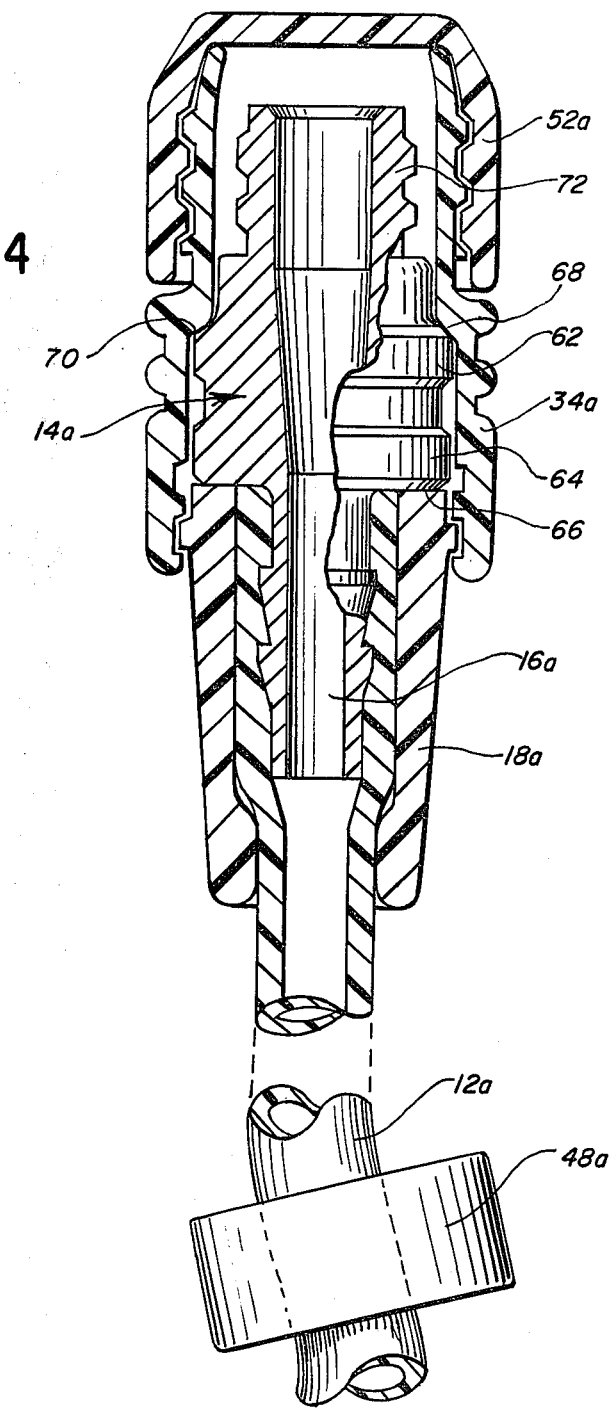
FIG. 4 is a longitudinal view taken mostly in section of another embodiment of the closure system of this invention.

Referring to FIG. 4, a modified embodiment of this invention is provided. Tubing 12a connects as before to a connector 14a, retained by projecting tube 16a as in the previous embodiment. Connector 14a may be made of titanium in this particular embodiment, being particularly useful as part of a set which communicates at its other end with a peritoneal catheter, with titanium connector 14a being for repeated connection and disconnection with peritoneal dialysis solution transfer sets, and/or containers.

Handle member 18a is shown, being of similar design to the previous embodiment and comprising a pair of hinged halves which may snap closed. Tubular closure member 34a is also disclosed, terminating in an end cap 52a, of similar design to the prior analogous structures.

In this embodiment, titanium adaptor 14a defines a pair of circumferential flanges 62, 64. Rear flange 64 defines a rear annular shoulder face 66 which one end of the handle member 18a abuts against to provide an annular seal of a type similar to that shown in the previous embodiment. Front flange 62 defines front shoulder face 68, which enters into sealing, abutting relation with annular internal seat 70 of connector 34a, to provide the annular internal seal of the type previously described.

In the alternative, the internal shoulder area may be formed in handle member 18a for sealing interaction with rear annular shoulder face 66, while the front annular shoulder face may abut against an end of tubular closure member 34a. Pinch clamp 48a is also provided, serving a purpose similar to that of the previous embodiment.

As shown, the closure system of this invention provides a spaced area preferably about 0.5 cm. from the end of the conduit end 72 so that antiseptic can bathe both the inner and outer surfaces of conduit end 72. The antiseptic is sealed within the closure of this invention by cap 52a, and an annular seal line is defined between members 68, 70. Thus the antibacterial effect of this system continues during storage, for example during the "dwell" phase of CAPD while peritoneal dialysis solution is residing in the patient between changes of peritoneal dialysis solution. This can result in a significant reduction in the cases of peritonitis which may take place due to accidental contamination of the system during connection and disconnection of peritoneal dialysis solution containers and/or transfer sets.

Figure 5:
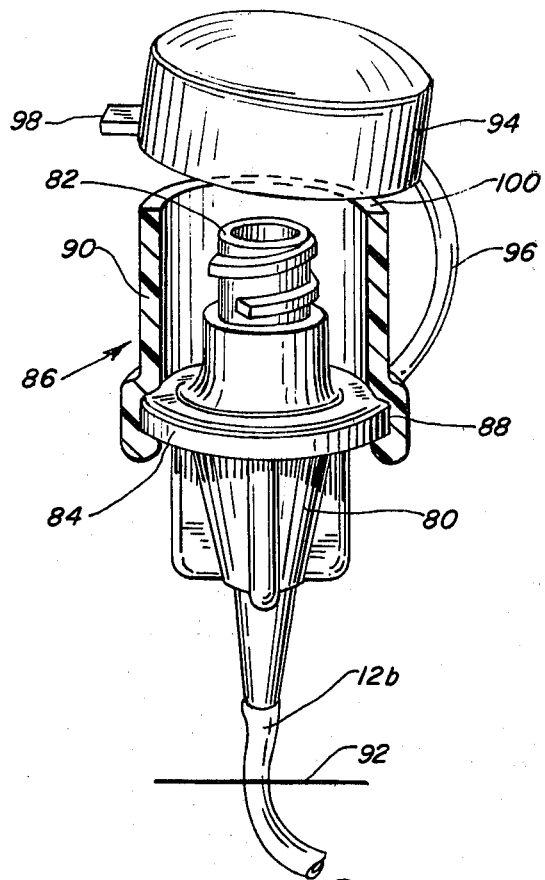
FIGS. 5 and 6 are elevational views, taken partly in section, of other embodiments of the closure system of this invention.

Referring to FIG. 5, a simplified embodiment of the closure system of this invention is provided. Flexible tubing 12b defines a connector 80 at its end having a threaded tubular connection 82 and an annular flange 84.

A one-piece, tubular elastomeric cap member 86 is provided having an annular groove 88 that enters into snapfit relation with flange 84 in tight, sealing manner. Tubular closure member 90 encloses the threaded tubular end 82 of the connector in spaced relation so that a liquid antiseptic such as povidone iodine may be poured into the bore of connector 80 and may bathe tubular end 82 within the chamber defined by flange 88 and closure member 90. A slide clamp 92 or other clamp member may be provided in a manner similar to the previous embodiments.

Cap 94 may be an integrally molded part of cap member 86, being connected to tubular closure member 90 by means of integral hinge 96. Cap 94 may have a gripping tab 98, and fits in tight, sealing manner about the outer lip 100 of closure member 90 so that liquid antiseptic may be retained within the closure system 86 in sealed manner.

Figure 6:
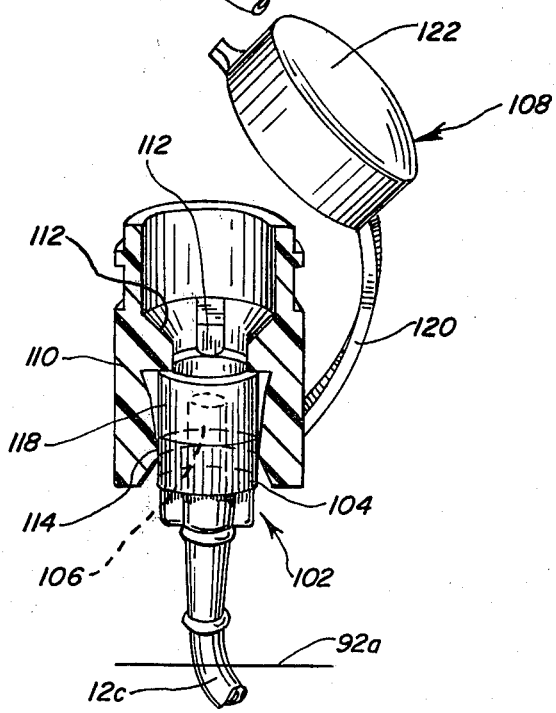

Referring to FIG. 6, flexible conduit 12c may be sealed with a slide clamp 92a and terminated with a connector member 102. Connector member 102 may include an outer sleeve 104 and an inner sleeve 106 which communicates with flexible conduit 12c.

Closure member 108 may once again be a one-piece, integrally molded elastomeric member comprising a tubular closure member 110 having radially inwardly projecting stop members 112 to limit the extent of advance of connector 102 into the closure member.

An interference ring 114 projects inwardly on the order of 0.02 inch around the lower edge of tubular closure member 110, being proportioned to provide a tight seal and also an annular space 118, which is also on the order of 0.02 inch width, to permit antiseptic to flow about the outer surface of tube 104 down to interference ring 114 which may be, for example, 1/16 of an inch wide.

As before, antiseptic may be poured into tubular closure 110 to fill tube 104 and bathe the outside of the endmost portion of the conduit (tube 106), and also to enter the bore of tube 106 and flexible conduit 12c, its degree of penetration being limited by slide clamp 92a.

Integral hinge 120 secures cap 122, which may be of similar design to the previous cap 94, for sealing the closure.

The one-piece closure members of FIGS. 5 and 6 may be made of any desired elastomeric material, for example silicone rubber or a formulation based on Kraton G block copolymer sold by the Shell Chemical Company.

The above has been offered for illustrative purposes only, and is not intended to limit the scope of the invention of this application, which is as defined in the claims below.

That which is claimed is:

1. A closure system for a conduit carrying a connector at its end said connector defining a forward end segment which closure system comprises a flexible, tubular closure member positioned about said connector in sealing relation thereto, said closure member being proportioned to telescope over said connector and defining a groove adapted for snap-fit relation with a projecting flange on said connector and defining annular sealing means for providing a seal between the flexible, closure member and connector, said closure member being spaced from said forward end segment, said closure member carrying a removable cap for access to the system and adapted for enclosing antiseptic which is in contact with both the interior and exterior of said connector and wherein said closure member and removable cap are in a one-piece, molded elastomeric structure, means for limiting the forward penetration of said connector into said closure member, the inner diameter of the flexible structure telescoped around the connector being proportioned to define a space to permit the penetration of antiseptic about a portion of the exterior forward portion of said connector for improved antibacterial effect on the connector.

2. The closure system of claim 1 in which said tubular closure member is spaced from at least 0.5 centimeter of the end portion of said connector.

3. A closure system for a conduit defining a connector at its end, said connector defining at least a first exterior annular sealing face, said closure system including:
a hollow, tubular handle member having screw thread means;
a tubular closure member, the rear end of said closure member defining screw thread means, proportioned to mate in closing relation with the screw thread means of the handle member, said closure member defining means to sealingly press against said sealing face when in closing relation with the handle member, the closure member surrounding but being spaced from the forward portion of said connector;
said handle member comprising a pair of hinged halves and proportioned to close about the rear portion of said connector in surrounding relation; and
end closure means to sealingly close the forward end of said tubular closure.

4. The closure system of claim 3 in which a forward portion of the handle member defines said screw thread means, said connector defining a second exterior, annular sealing face, said handle member being proportioned to sealingly press against said second exterior annular sealing face.

5. The closure system of claim 4 in which said hollow, tubular handle member defines a front end which is proportioned to sealingly press against said second sealing face, while the tubular closure member defines an inner, annular seat proportioned to sealingly press against said first sealing face of the connector.

6. The closure system of claim 3 in which said hollow, tubular handle member and tubular closure member are joined together by said screw thread means in sealing relation with the connector and said end closure means is in sealingly closed position.

7. The closure system of claim 6 in which said end closure means comprises a separate cap member proportioned for removable sealing relation with the forward end of the tubular closure.

8. The closure system of claim 3 in which means are provided for removably sealing the bore of said conduit at a position adjacent to but spaced from said connector.

9. The closure system of claim 3 in which said hollow, tubular handle member defines a pair of opposed, flat, exterior faces proportioned to facilitate manual grasping thereof.

10. The closure system of claim 3 in which said connector defines at its end inner and outer spaced, concentric telescoping sleeves, said inner sleeve constituting an extension of the conduit, said outer sleeve surrounding and extending out beyond said inner sleeve, said outer sleeve also defining on its inner surface screw threads for entering into sealing, locking relation with another connector, whereby said screw threads of the outer sleeve are exposed to contact with antiseptic placed within said closure system sealingly carried about said connector.

11. The closure system of claim 3 in which said handle member, tubular closure member, and end closure are locked together about a connector, and enclose liquid antiseptic therein to bathe the end of said connector for antibacterial effect, the bore of said conduit being removably sealed at a location spaced from but adjacent to said connector.

12. A closure system for a conduit defining a connection at its end, said connector defining at least a first exterior, circumferential annular sealing face, said closure system including:
a hollow, tubular handle member comprising a pair of hinged halves and closed about the rear portion of said connector in surrounding relation;
a tubular closure member, the rear end of said closure member mating in closing relation with the handle member, said closure member defining means sealingly pressing against the annular sealing face when in closing relation with the handle member, said closure member surrounding but being spaced from the forward portion of said connector, and end closure means to sealingly close the tubular closure member, there being antiseptic present within said tubular closure in contact with both the bore of said connector and exterior end portions thereof, the bore of said conduit being removably sealed at a position adjacent to but spaced from said connector.

13. The closure system of claim 12 in which said hollow, tubular handle member defines a front end which is proportioned to sealingly press against the annular sealing face while the tubular closure member defines an inner, annular seat proportioned to sealingly press against another annular face of the connector.

14. The closure system of claim 13 in which said hollow, tubular handle member defines a pair of opposed, flat, exterior faces proportioned to facilitate manual grasping thereof.

15. The closure system of claim 24 in which said end closure means comprises a separate cap member proportioned for removable sealing relation with the forward end of the tubular closure.

16. The closure system of claim 13 in which said connector defines at its end inner and outer spaced, concentric telescoping tubes, said inner tube constituting an extension of the conduit, said outer tube surrounding and extending out beyond said inner tube, the outer tube also defining on its inner surface screw threads for entering into sealing, locking relation with another connector, whereby said screw threads on the outer tube are exposed to contact with the antiseptic within said closure system sealingly carried about said connector.

17. The closure system of claim 16 in which said connector defines radially projecting vanes, said handle member defining an inner aperture of a cross section which defines corners positioned and proportioned to receive the vanes of said connector positioned within the handle means, whereby the handle member and connector are positioned together in nonrotatable relation.

* * * * *